United States Patent [19]

Groh

[11] Patent Number: 5,863,943
[45] Date of Patent: Jan. 26, 1999

[54] STABILIZED SKIN CONDITIONER WITH ALPHA HYDROXY ACIDS

[75] Inventor: David G. Groh, Temecula, Calif.

[73] Assignee: The Andrew Jergens Company, Cincinnati, Ohio

[21] Appl. No.: 867,821

[22] Filed: Jun. 3, 1997

[51] Int. Cl.$^6$ ...................................... A61K 31/19
[52] U.S. Cl. .......................... 514/557; 514/558; 514/938; 424/59
[58] Field of Search .................................... 514/114, 557, 514/938

[56] References Cited

U.S. PATENT DOCUMENTS 4,209,449  6/1980  Mayhew et al. ......................... 260/403
5,567,427  10/1996  Papadakis ............................... 424/401

*Primary Examiner*—Leonard Schenkman
*Attorney, Agent, or Firm*—Oblon, Spivak, McClelland, Maier & Neustadt, P.C.

[57] ABSTRACT

An improved skin conditioner, incorporating alpha hydroxy acids, is an emulsion stabilized by the combination of a high molecular weight polyethylene glycol and a quaternary ammonium salt phosphate cationic surfactant, specifically, an alkyl amidopropyl PG-Dimonium Chloride phosphate type cationic surfactant. The composition may include other active agents, non-ionic emulsifying surfactants, emollients and additives. The resulting composition has a desirable "feel" and storage stability, even at relatively high temperatures.

8 Claims, No Drawings

STABILIZED SKIN CONDITIONER WITH ALPHA HYDROXY ACIDS

BACKGROUND OF THE INVENTION

1. Field of the Invention

This invention pertains to skin conditioning compositions which comprise relatively high loadings of alpha hydroxy acids in a stabilized, aesthetically pleasing form. Specifically, these compositions are emulsions stabilized by a complex of polyethylene glycol (PEG) and a cationic surfactant.

2. Background of the Prior Art

It is well established that alpha hydroxy acids have a variety of utilities in connection with skin conditioning. Alpha hydroxy acids have been documented in the treatment of a variety of skin conditions having to do with keratinazition, see U.S. Pat. Nos. 5,091,171 and 4,363,815. U.S. Pat. No. 5,618,850 describes problems encountered in connection with use of these acids in skin treatments, including problems resulting from lack of stabilization of the vehicle incorporating them. U.S. Pat. No. 5,616,332 describes the preparation of a variety of cosmetic and pharmacological formulations employing alpha hydroxy acids (AHA's). U.S. Pat. No. 5,621,006 describes the use of certain alpha hydroxy acids and related compounds for topical treatment of a variety of skin disorders.

Although the application of alpha hydroxy acids at significant loadings has been documented as having value in the treatment of skin conditions, as noted, the delivery of these acids to the skin in appropriate amounts is problematical. One particular difficulty encountered is the stabilization of conventional oil-in-water (O/W) emulsions, which, due in part to the acidic nature of the preparation, are unstable, have a relatively short shelf life, and upon storage, tend to develop an aesthetically unpleasant character. Further, to achieve the best possible skin treatment (treatment can broadly encompass addressing specific skin disorders, moisturizing, de-keratinazition, etc.) it is desirable to provide a preparation, such as a lotion or creme, which is resistant to be washed off upon rinsing of the skin. Such compositions are addressed in U.S. Pat. No. 5,013,763, for delivery of agents other than alpha hydroxy acids. Other formulations are described in U.S. Pat. No. 4,389,418.

Other skin conditioning active agents are known. As one example, various oatmeal preparations, oatmeal extracts and the like, are known to provide a soothing skin effect. The delivery of oatmeal in a stable O/W emulsion itself presents stability problems.

Accordingly, it remains an object of those of ordinary skill in the art to provide a skin conditioning treatment, an O/W emulsion, which is stable, is a suitable carrier for one or more AHA, is a suitable carrier for topically active agents such as sunscreens, and the like.

SUMMARY OF THE INVENTION

The above objects, and others set forth in more detail below, are met by the provision of a stabilized O/W cationic emulsion comprising at least one AHA, which is stabilized by the incorporation of a high molecular weight PEG complexed with a cationic surfactant. Specifically, PEG's of approximately 100,000–4,000,000 molecular weight (weight average), when combined with a cationic surfactant of the R-amidopropyl PG-Dimonium Chloride Phosphate type lends the emulsion a high degree of stability, even under adverse conditions, and provides a suitable skin conditioning vehicle for the delivery of AHA, oatmeal, and other active agents.

The invention is premised on the discovery that the stabilizing effect is narrowly limited to high molecular weight PEG and specific phosphate quaternary ammonium salts of the R-amidopropyl PG-Dimonium Chloride phosphate type. Use of related polymers, or related cationic surfactants, does not provide stability or aesthetic effects.

DETAILED DESCRIPTION OF THE INVENTION

A primary active agent of the inventive compositions is an AHA. A wide variety of these acids are known to those of skill in the art, and can be used in this invention. Alkyl alpha hydroxy acids are preferred, generally mono and di alkyl AHAs with R groups of 1–18 carbon atoms, and include 2-hydroxyethanioc acid (glycolic acid), 2-hydroxypropanioc acid (lactic acid), 2-methyl 2-hydroxypropanioc acid (methyl lactic acid), 2-hydroxybutanioc acid, 2-hydroxypentanioc acid and related hydroxyalkanoic acids C6 (2-hydroxyhexanioc acid) - C18 (2-hydroxyoctadecanioc acid or alpha hydroxystearic acid). Preferred alpha hydroxy acids include glycolic and lactic acid.

The essential elements that constitute the delivery system for the AHA are water and an oil phase to form the basic emulsion, with mineral oil and other conventional oleaginous cosmetic bases being suitable for the oil phase, PEG 100,000–4,000,000, and a cationic phosphate surfactant of a quaternary ammonium salt. The cationic surfactant has the formula

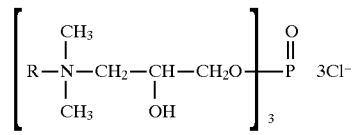

Wherein each R is independently stearyl, linoleyl or cocoyl. The PEG and cationic surfactant apparently complex, in a method not clearly understood, to provide a stabilizing, aesthetically pleasing effect for the emulsion.

Although a wide variety of additives and additional active agents may be provided, broadly, the alpha hydroxy acid is present in amounts of 1–12%, by weight of the composition. Amounts below 1%, while acceptable, may not yield advantageous skin enhancement effects credited to alpha hydroxy acids.

The non-aqueous phase of this skin conditioning emulsion may be natural or synthetic. It constitutes the moisturizing or emollient elements of the emulsion. Examples include straight chain hydrocarbons of about 10–40 carbon atoms, generally referred to as mineral oils. Branched chain hydrocarbons, having from about 10 to as many as 200 carbon atoms may also be used, depending on adjustments made in the remaining components for desired viscosity. Among branched chain hydrocarbons of this type that may be considered are polydecenes, polyisobutenes, hydrogenated polyisobutenes, squalane and squalene. Mixtures of these oils can of course be used. Natural mineral oil is generally preferred. Non-aqueous emollients other than traditional oils may also be used as all or part of the non-aqueous phase. These moisturizing or emollient compounds may include one or more of a fatty acid ester, branched chain fatty alcohol or acid, or silicone. The fatty acid esters, alcohols and acids typically have 8–40 carbon atoms. Suitable fatty acid esters include fatty acids of monohydric alcohols of the general formula $R_1$—O—CO—$R_2$, wherein $R_1$, and $R_2$ are hydro-carbon chains derived from animal and/or vegetable fats and oils, or petroleums. Examples include isopropyl palmitate, octyl isononanoate, myristyl neopentanote, isodecyl oleate, cetyl octanoate, etc. Fatty esters of ethoxylated monohydric alcohols may also be employed. Examples include myreath-3, laureth-2 octanoate, myreath-3 myristate, etc.

Di- and tri-esters of the monohydric alcohols of the type discussed above may also be employed, including diisopropyl adipate, triisostearyl trilinoleate, trioctyl citrate, and others. Similarly, branched chain fatty alcohols or acids may be used if soluble in the hydrocarbon oil component. Representative members of this class include isostearic acid, butyl octanol, decyl dodecanol, etc.

Suitable non-aqueous phase elements also comprise non-oil emollients including synthetic liquid silicone polymers of the formula

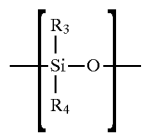

Wherein $R_3$ and $R_4$ are lower alkyls of 1–6 carbon atoms. Examples include dimethicone, dimethiconiol and cyclomethicone. The non-aqueous phase, preferably mineral oil, is present in an amount of 10–35% by weight. Amounts below about 10% give inadequate moisturizing, while amounts in excess of 35% leave a greasy, undesirable feeling on the skin.

The polyethylene glycol is present in amounts of 0.01–5%, by weight of the composition. The amount of polyethylene glycol is adjusted, given the amount of AHA and oil phase present, to provide adequate stabilizing effect.

The cationic surfactant of the formula set forth above is present in amounts greater than the PEG, and generally 0.05–15%, by weight. Water constitutes the balance of essential ingredients.

Additional active agents can be added to the emulsion, for the purposes of topical treatment. Among these are chemical and physical sunscreens such as octyl methoxycinnamate, benzophenone-3, titanium dioxide, zinc oxide, PABA and derivatives, as well as others such as oatmeal. Other suitable active agents include skin protectants such as dimethicone, allantoin, etc., bactericides, fungicides, aesthetics, etc. Additionally, topical pharmaceuticals may be added. Representative agents include anti-acne agents such as benzoyl peroxide, anti-inflammatory agents like hydrocortisone, vasodilators such as histamine hydrochloride and methyl nicotinate, and anesthetics like benzocaine. These may be present in amounts up to about 5% by weight, sufficient to achieve the desired result.

The composition advantageously also employs additional non-ionic emulsifying surfactants, such as glyceryl stearate, steareth-21, steareth-2 and conventional emulsifying stabilizers such as cetearyl alcohol.

As additional elements, conventional cosmetic additives may be added to the skin treatment composition. Principle additives include fragrances, anti-oxidants, preservatives, and pigments or colorants. These are generally present in amounts necessary to provide the desired effect, generally between 0.01 and 5%, by weight of the composition.

Stability

The inventive composition, generally a lotion or a creme, achieves improved aesthetics and improved high temperature stability by incorporation of one or more high molecular weight PEGs. In general, the molecular weight should range from about 100,000–4,000,000, with a preferred range being 500,000–2,000,000. This stabilizing effect is dependent on the selection of the cationic surfactant of formula I. These phosphate type cationic surfactants are commercially available from Mona Industries under the name Phospholipid SV, EFA, GLA, PTC and CDM. The stabilizing effect appears to be based on a formation of a complex between the two components, the details of which are not clearly understood. Nonetheless, selection of the PEG stabilizer and cationic surfactant appear to be essential for stabilization. Other polymers commonly employed for aesthetic feel and stability, such as hydroxyethylcellulose and xanthan gum do not provide the stability necessary. Similarly, even if PEG is selected, closely related cationic surfactants, such as isostearylamidopropyl PG-Dimonium Chloride and Distearyl Dimonium Chloride do not provide stability, and gave an undesirable aesthetic appearance. This surprising selectivity of stabilizer and cationic surfactant is reflected in the data set forth in Table 1 herewith, which reflect the superior stabilizing effect of the combination of PEG of varying molecular weight and cationic surfactants of formula I.

To prepare the inventive composition, the components are mixed together according to conventional means. Thus, a water phase, which includes in addition to water, the AHA, other water miscible active agents as desired and PEG are mixed together to dissolve, or prepare a thorough and stable suspension. The cationic surfactant of formula I is added to this phase. Typically, the phase is heated to a temperature of about 75°–95° C., before being added to the oil phase. The non-aqueous phase incorporates the emollients and moisturizing agents such as mineral oil, emulsifying surfactants if included, and hydrophobic additives as desired. When heated to the temperature of the water phase, the two phases are mixed together. If necessary, additional lactic acid is added with water, together with sodium hydroxide, to achieve appropriate pH. Conventional mixing procedures are employed.

TABLE 1

| | | Comparative Examples % (wt./wt.) | | | | | | |
|---|---|---|---|---|---|---|---|---|
| Supplier/Ref. No. | Raw Material Description | 937C150 | 937C155 | 937C157 | 937C174 | 937C176 | 937C163 | 971003 |
| 8390-00-020 | DI Water | 61.66 | 65.41 | 58.76 | 56.78 | 57.28 | 61.06 | 55.15 |
| 9672-00-020 | Lactic Acid | 5.00 | 5.00 | 5.00 | 5.00 | 5.00 | 3.00 | 5.00 |
| 8026-00-020 | NaOH (50%) | 1.00 | 1.00 | 1.50 | 1.60 | 1.60 | 1.60 | 1.60 |
| 9717-00-020 | Oatmeal Extract | 0.10 | 0.10 | 0.10 | | | 0.10 | 0.01 |
| Multiple | Humectant | 8.00 | 8.00 | 8.00 | 8.00 | 5.00 | 8.00 | 7.00 |
| 9656-00-020 | Xanthan Gum | | 0.25 | 0.50 | | | | |
| Aqualon HHR-250 | Hydroxyethylcellulose | | | | 0.25 | 0.25 | | |

TABLE 1-continued

| Supplier/Ref. No. | Raw Materials Description | | | | | | | |
|---|---|---|---|---|---|---|---|---|
| Union Carbide WSR N-60K | PEG-45M (MW 2,000,000) | | | | | | | 0.10 |
| Union Carbide WSR N-10 | PEG-2M (MW 100,000) | | | | | | | |
| Union Carbide WSR N-3000 | PEG-14M (MW 600,000) | | | | | | | |
| Union Carbide WSR 301 | PEG-90M (MW 4,000,000) | | | | | | | |
| Inoion Louquat AMG | Isostearylmidopropyl PG-Dimonium Chloride | | | | 5.00 | | | 4.00 |
| Mono Phospholipid SV | Stearamidopropyl PG-Dimonium Chloride Phosphate | | 3.00 | 4.00 | | 3.00 | 3.00 | |
| Mono Phospholipid GLA | Borageamidopropyl PG-Dimonium Chloride Phosphate | | | | | | | |
| Mono Phospholipid EFA | Ilnoleamidopropyl PG-Dimonium Chloride Phosphate | | | | | | | |
| 9622-00-020 | Distearyl Dimonium Chloride | 1.00 | | | | | | |
| 9620-00-020 | Cetearyl Alcohol | 2.60 | 2.60 | 3.00 | 3.00 | 3.00 | 3.00 | 3.50 |
| 9640-00-020 | Glyceryl Stearate | | | | 1.75 | 1.75 | | 1.00 |
| 8242-00-020 | Glyceryl Stearate & PEG100 St | 3.00 | | | | 5.00 | | 5.00 |
| ICIBr‖721S | Steareth-21 | | | 0.25 | 3.75 | | 1.20 | |
| ICIBr‖72 | Steareth-2 | | | 1.25 | 0.25 | | 1.20 | |
| Multiple | Oil Phase | 17.04 | 14.04 | 17.04 | 14.02 | 17.52 | 17.04 | 17.04 |
| Multiple | Preservatives | 0.60 | 0.60 | 0.60 | 0.60 | 0.60 | 0.60 | 0.60 |
| | Total | 100.00 | 100.00 | 100.00 | 100.00 | 100.00 | 100.00 | 100.00 |
| | Initial Appearance | Grainy | Grainy | Grainy | Grainy | Grainy | Grainy | Smooth |
| | Initial Particle Size (micrometers) | na | na | na | 5 to 10 | <1 | na | 2 to 6 |
| | Initial Viscosity (Centipoise) | na | na | na | na | na | na | na |
| | Initial pH | na | na | na | 3.63 | na | na | na |
| | Stability Comments | unstable | unstable | unstable | unstable | Grainy @ 1 wk 60° C. | Separation 4 wk 60° C. | Separation 1 wk 60° C. |

| | | Inventive Composition % (wt./wt.) | | | | | | | |
|---|---|---|---|---|---|---|---|---|---|
| Supplier/Ref. No. | Raw Materials Description | 971004 | 971066 | 971087 | 971092 | 971093 | 971094 | 971170 | 971171 |
| 8390-00-020 | DI Water | 59.40 | 60.90 | 60.90 | 60.90 | 60.90 | 60.90 | 60.95 | 60.98 |
| 9672-00-020 | Lactic Acid | 5.00 | 5.00 | 5.00 | 5.00 | 5.00 | 5.00 | 5.00 | 5.00 |
| 8026-00-020 | NaOH (50%) | 1.60 | 1.60 | 1.60 | 1.60 | 1.60 | 1.60 | 1.60 | 1.60 |
| 9717-00-020 | Oatmeal Extract | 0.01 | 0.01 | 0.01 | 0.01 | 0.01 | 0.01 | 0.01 | 0.01 |
| Multiple | Humectant | 7.00 | 5.50 | 5.50 | 5.50 | 5.50 | 5.50 | 5.50 | 5.50 |
| 9656-00-020 | Xanthan Gum | | | | | | | | |
| Aqualon HHR-250 | Hydroxyethylcellulose | | | | | | | | |
| Union Carbide WSR N-60K | PEG-45M (MW 2,000,000) | 0.10 | 0.10 | 0.10 | | | | 0.050 | 0.025 |
| Union Carbide WSR N-10 | PEG-2M (MW 100,000) | | | | 0.10 | | | | |
| Union Carbide WSR N-3000 | PEG-14M (MW 600,000) | | | | | 0.10 | | | |
| Union Carbide WSR 301 | PEG-90M (MW 4,000,000) | | | | | | 0.10 | | |
| Inoion Louquat AMG | Isostearylmidopropyl PG-Dimonium Chloride | | | | | | | | |
| Mono Phospholipid SV | Stearamidopropyl PG-Dimonium Chloride Phosphate | 3.25 | | | | | | 3.25 | 3.25 |
| Mono Phospholipid GLA | Borageamidopropyl PG-Dimonium Chloride Phosphate | | | 3.25 | 3.25 | 3.25 | 3.25 | | |
| Mono Phospholipid EFA | Ilnoleamidopropyl PG-Dimonium Chloride Phosphate | | 3.25 | | | | | | |
| 9622-00-020 | Distearyl Dimonium Chloride | | | | | | | | |
| 9620-00-020 | Cetearyl Alcohol | 3.00 | 3.00 | 3.00 | 3.00 | 3.00 | 3.00 | 3.00 | 3.00 |
| 9640-00-020 | Glyceryl Stearate | 0.50 | 0.50 | 0.50 | 0.50 | 0.50 | 0.50 | 0.50 | 0.50 |
| 8242-00-020 | Glyceryl Stearate & PEG100 St | 5.00 | 5.00 | 5.00 | 5.00 | 5.00 | 5.00 | 5.00 | 5.00 |
| ICIBr‖721S | Steareth-21 | | | | | | | | |
| ICIBr‖72 | Steareth-2 | | | | | | | | |
| Multiple | Oil Phase | 14.54 | 14.54 | 14.54 | 14.54 | 14.54 | 14.54 | 14.54 | 14.54 |

TABLE 1-continued

| Multiple | Preservatives | 0.60 | 0.60 | 0.60 | 0.60 | 0.60 | 0.60 | 0.60 | 0.60 |
|---|---|---|---|---|---|---|---|---|---|
| | Total | 100.00 | 100.00 | 100.00 | 100.00 | 100.00 | 100.00 | 100.00 | 100.00 |
| | Initial Appearance | Smooth | Smooth | Smooth | Smooth | Smooth | Smooth | Smooth | Smooth |
| | Initial Particle Size (micrometers) | <3 | 2 to 3 | 2 to 3 | 15 to 20 | <5 | <2.5 | <3 | 3 to 6 |
| | Initial Viscosity (Centipoise) | 135,000 | 40,000 | 41,000 | 60,000 | 81,000 | 85,000 | 78,000 | 71,000 |
| | Initial pH | 3.60 | 3.70 | 3.69 | 3.62 | 3.64 | 3.60 | 3.68 | 3.62 |
| | Stability Comments | Pass 12 wk. 60° C. | Pass 4 wk 60° C. | Pass 4 wk 60° C. | Grainy @ 4 wk 60° C. | Pass 4 wk 60° C. | Pass 4 wk 60° C. | Pass 4 wk 60° C. | Grainy @ 4 wk 60° C. |

The composition described is gentle, notwithstanding the use of cationic surfactants, and of acidic pH (approximately 4.0–6.0), suppressing any "amine" smell and consistent with natural skin pH. It is thus suitable for application to any portion or portions of human skin, as an effective vehicle for skin conditioning, per se, including skin moisturizing and softening, as well as the various effects of the AHA and other active agents incorporated.

The invention has been described both generically, and by reference to specific example. The examples are not limiting, and alternatives will occur to those of ordinary skill in the art without the exercise of inventive faculty. In particular, the selection of other hydrocarbons, active agents, additives, emollients and the like, as well as the adjustment of the various range of components, will occur to those of ordinary skill in the art, without departing from the spirit of the invention, which is limited only by the recitations of the claims set forth below.

What is claimed is:

1. A skin conditioning composition, comprising:
   (a) an alpha hydroxy acid in an amount of 1.0–12%, by weight of the composition,
   (b) a non-aqueous moisturizing component in an amount of 10–35%, by weight of the composition comprising natural or synthetic hydrocarbons of 10–200 carbon atoms, fatty acid esters of branched chain fatty alcohols, branched chain fatty acids, silicones and mixtures thereof,
   (c) polyethylene glycol (PEG) of molecular weight of 100,000–4,000,000,
   (d) a cationic surfactant of the formula

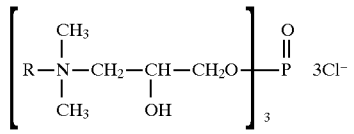

wherein each R is independently stearyl, linoleyl or cocoyl, and
   (e) water, said components (b)–(d) being present in amounts effective to provide a stable emulsion.

2. The composition of claim 1, wherein said PEG has a molecular weight of 500,000–2,000,000.

3. The composition of claim 1, wherein said composition further comprises emulsifying non-ionic surfactants.

4. The composition of claim 1, wherein said composition further comprises a chemical or physical sunscreen.

5. The composition of claim 1, wherein said composition further comprises an active agent selected from the group consisting of oatmeal, a bactericide, fungicide, and a pharmaceutical.

6. The composition of claim 1, wherein said AHA is lactic acid, glycolic acid or a combination thereof.

7. The emulsion of claim 1, wherein said emulsion is stable on storage for at least 12 weeks at 50° C.

8. A method of treating human skin, comprising applying an effective amount of the composition of claim 1 to said skin, and allowing it to remain there for a time sufficient to effect the condition of said skin.

* * * * *